United States Patent [19]

Hillstead

[11] Patent Number: 5,423,762
[45] Date of Patent: Jun. 13, 1995

[54] MODULAR CATHETER SHEATH INTRODUCER

[75] Inventor: Richard A. Hillstead, Duluth, Ga.

[73] Assignee: Cordis Corporation, Miami Lakes, Fla.

[21] Appl. No.: 47,847

[22] Filed: Apr. 15, 1993

[51] Int. Cl.⁶ ............................................. A61M 5/178
[52] U.S. Cl. ..................... 604/167; 604/256; 604/283; 604/53
[58] Field of Search ............... 604/164, 167, 171, 256, 604/264, 283, 28, 49, 53, 280

[56] References Cited

U.S. PATENT DOCUMENTS

| | | | |
|---|---|---|---|
| 4,430,081 | 2/1984 | Timmermans | 604/167 |
| 4,436,519 | 3/1984 | O'Neil | 604/256 |
| 5,009,391 | 4/1991 | Steigerwald | 604/167 |
| 5,167,644 | 12/1992 | Fischell et al. | 604/264 |
| 5,207,656 | 5/1993 | Kranys | 604/167 |

FOREIGN PATENT DOCUMENTS

| | | | |
|---|---|---|---|
| 1106 | 3/1979 | European Pat. Off. | 604/283 |
| 9110459 | 7/1991 | WIPO | 604/167 |

Primary Examiner—John G. Weiss
Attorney, Agent, or Firm—Gerstman, Ellis & McMillin, Ltd.

[57] ABSTRACT

A catheter sheath introducer comprises: a tubular body portion having opposed ends; a catheter sheath tube which is optionally replaceably carried on one of the body portion ends; and a slit, elastomeric hemostasis valve partition which is optionally replaceably carried on the other of the body portion ends.

11 Claims, 1 Drawing Sheet

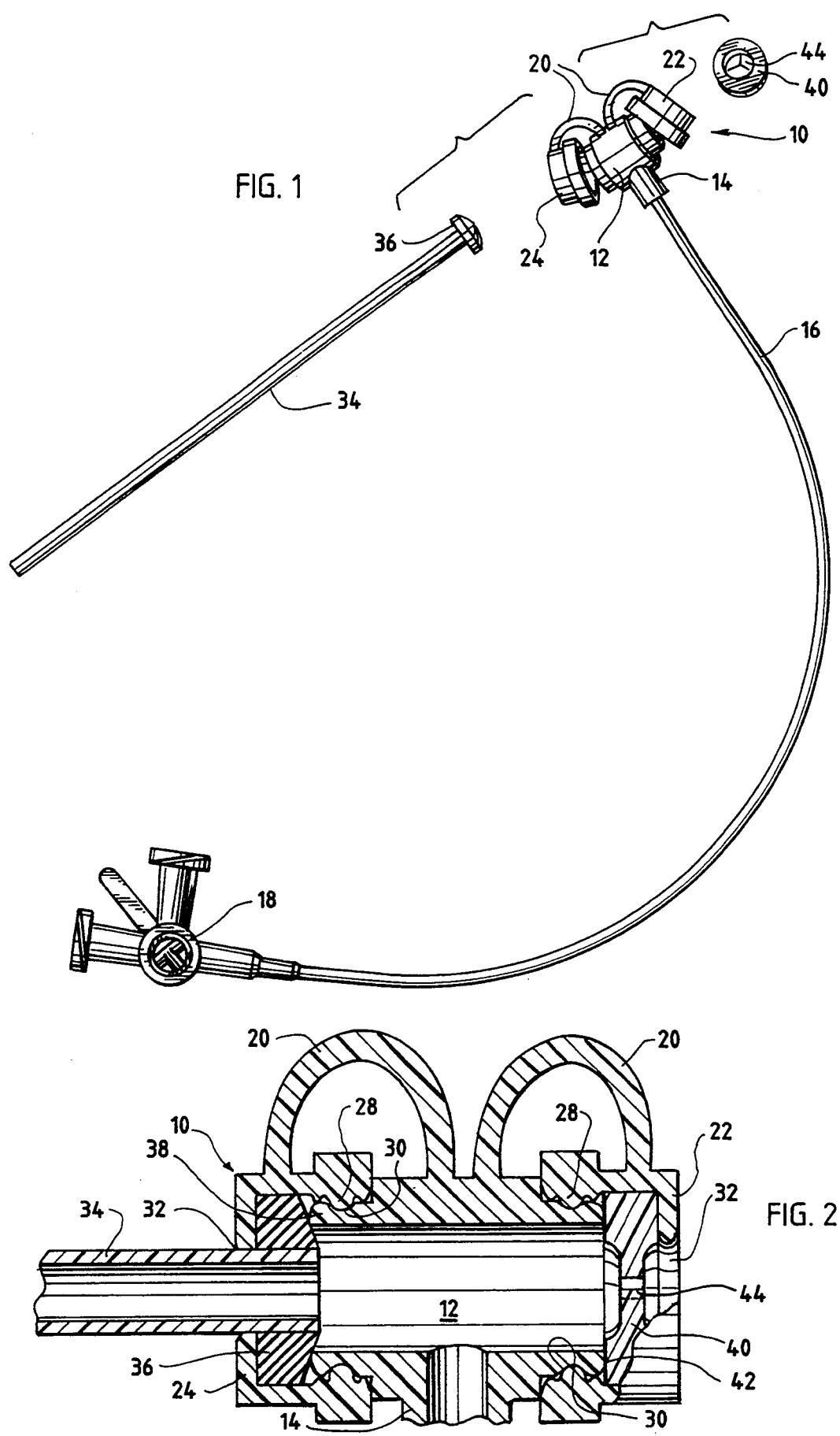

MODULAR CATHETER SHEATH INTRODUCER

BACKGROUND OF THE INVENTION

As described for example in Stevens U.S. Pat. Nos. 4,000,739, 4,421,296 and elsewhere, catheter sheath introducers are disclosed for the purpose of providing access by catheters to the arteries of a patient for purposes such as percutaneous translumenal coronary angioplasty (PTCA) and other surgical procedures. The catheter sheath introducer defines a housing from which extends a flexible tube portion having a length on the order of six inches, which tube portion is surgically emplaced into the artery of a patient. Then, catheters may be inserted and withdrawn through the tube portion for access, often by several different catheters in succession, to the arterial system of the patient without creating undue abrasion injury at the access site.

Also, the housing of the catheter sheath introducer is tubular, with a proximal portion thereof being obstructed by an elastomeric barrier which defines a slit. This elastomeric barrier serves as a hemostasis valve to limit or prevent the backflow of blood from the artery out of the proximal end of the catheter sheath introducer, while at the same time permitting catheters to be advanced through the introducer. One of numerous examples of such a slit elastomeric barrier for use in a catheter sheath introducer is disclosed in the cited Hillstead U.S. Pat. Nos. 4,895,565 and 4,798,594.

In PTCA and other surgical procedures, the surgeon may use varying sizes and types of catheters in the same procedure. Finding one catheter to be unsuccessful in performing the desired procedure, the surgeon may withdraw it through the catheter sheath introducer and replace it with another catheter. Also, there is a wide variety of catheters which may be used to enter the arteriovenous system of the patient, some of which catheters are more desirably used with certain types of catheter sheath introducers, and other catheters being more desirably used with other types of such introducers. Catheter sheath introducers may vary as to the type of elastomeric barrier valves used, the stiffness, diameter, and length of the sheath tube carried by the introducer, and the like. Thus, a well equipped hospital or clinic will have to stock a substantial number of different of catheter sheath introducers, which represents both a complexity in the control of inventory, and a tie-up of capital.

In accordance with this invention, a modular catheter sheath introducer is provided which may be modified in accordance with the immediate needs of the surgeon prior to the surgical procedure in a manner which depends upon the nature of the catheters expected to be inserted through the introducer. Thus, an improved flexibility of selection of a particularly desired catheter sheath introducer is provided, with a reduction in the amount of inventory stored by the hospital or clinic, to provided a maximum degree of flexibility of use to the surgeon at a minimum of inventory cost and administration.

DESCRIPTION OF THE INVENTION

In this invention, a catheter sheath introducer comprises a tubular body portion having opposed ends, a catheter sheath tube which may be replaceably carried on one of the body portion ends, and a slit, elastomeric hemostasis valve partition which may be replaceably carried on the other of the body portion ends.

As is typical for catheter sheath introducers, the body portion may also carry a laterally extending side port, for connection with plastic tubing for providing a saline solution or the like to flush the interior of the body portion and catheter sheath tube as desired by the surgeon.

Preferably, the catheter sheath tube may be connected at one end to first, snap-fit, sealing attachment means connected to the one body portion end. It is also preferred for the hemostasis valve partition to be carried in second, snap-fit, sealing attachment means connected to the other body portion end. Preferably, a tether is provided for each of the snap-fit sealing attachment means, so that such means are not mislaid or lost when they are separated from their snap-fit, sealing relation with the body portion. Also, in that circumstance, the body portion, the tethers, and the first and second snap-fit sealing attachment means which are present may all be integrally molded as a single piece. Thereafter, the catheter sheath tube and the elastomeric hemostasis valve partition may be added.

Thus, the surgeon may in effect "build" a desired catheter sheath introducer having a catheter sheath tube of a desired diameter, length and physical composition, typically combined with a particular elastomeric hemostasis valve partition having a slit size to accommodate the particular catheter or catheters used in the specific procedure. Thus, a wide inventory of catheter sheath introducers may be replaced with one or only a few body portion models. A variety of separate, attachable modular catheter sheath tubes and valve partitions provides the user with the best available type of catheter sheath introducer for the particular surgical procedure to be performed.

DESCRIPTION OF THE DRAWINGS

In the drawings, FIG. 1 is a plan view of a catheter sheath in accordance with this invention, in disassembled mode; and FIG. 2 is a fragmentary, longitudinal sectional view of the catheter sheath introducer of FIG. 1, showing the assembled mode.

DESCRIPTION OF SPECIFIC EMBODIMENTS

Referring to the drawings, a catheter sheath introducer 10 is shown, which is adapted to receive an inner catheter in the conventional manner for inserting into the vascular system of a patient, while preventing blood backflow along the outside of the inner catheter. Because the prior art designs of catheter sheath introducers are typically limited to a narrow range of only one or two French sizes of inner catheter for which they can provide effective entry and sealing, without removing too much lubricant from the inner catheter, catheter sheath introducer 10 is capable of modification to effectively receive and seal the desired inner catheter or catheters.

Catheter 10 comprises a tubular body portion 12, which carries a laterally extending side port 14 communicating in conventional manner with flexible plastic tubing 16 and three way valve 18, for the administration of saline solution and other known uses.

Tubular body portion 12 is made of any suitable plastic, being integrally molded with a pair of tether members 20, which are joined at one end to body portion 12. At their other ends each tether 20 is respectively joined to a separate, snap-fit sealing cap 22, 24. Each cap 22, 24 defines a rim having a snap-fit annular rib 28, which fits into a corresponding annular recess 30 defined in tubular body portion 12. Thus, the respective caps 22, 24 can be removed from their snap-fit engagement as shown in FIG. 1, or placed into snap-fit engagement as shown in FIG. 2. Each of snap-fit sealing cap members 22, 24 are shown to have a central aperture 32.

Accordingly, it becomes possible for the user of catheter sheath introducer 10 to select any desired model of a catheter sheath tube 34, which tube carries on one end thereof in sealed relation an apertured, fitting, resilient head 36, which is proportioned to fit inside of sealing cap 24 with catheter sheath tube 34 projecting through aperture 32. Also, head 36 is of a thickness and shape so that when sealing cap 24 is snapped into the closed position as shown in FIG. 2, an annular seal is defined between head 36 and the annular end 38 of body portion 12, to provide a desired seal. Nevertheless, if desired, sealing cap 24 may be removed from its seated configuration to permit replacement of catheter sheath tube 34 with another sheath tube 34 which may be of a different diameter, or a different length, or of different softness or other physical properties. Thus, the same catheter sheath introducer may be used in conjunction with a wide variety of catheters by the simple selection of an appropriate catheter sheath tube 34.

Similarly, a slit, elastomeric, hemostasis valve partition 40 may be selected from among a wide variety of candidates and inserted into snap-fit sealing cap 22 in the manner shown in FIG. 2. Sealing cap 22 may be snapped into place as shown, being proportioned so that cap 22 in its snap-fit retention exerts a pressure seal between cap 22 and annular end 42 of body 12, so as to compress valve partition 40 into sealed relation.

Then, after sheath introducer 10 has been emplaced in a patient with sheath tube 34 positioned in an artery of a patient, sealing partition 40 will prevent the backflow of blood out of aperture 32. However, a catheter can penetrate through the slit 44, which slit may be a pattern of slits of Y-shape or any other desired slit pattern, for example as disclosed in the previously cited Hillstead patents. A catheter thus slides through elastomeric partition 40, advancing through body 12 and sheath tube 34 into the artery of the patient without significant proximal blood leakage through catheter sheath introducer 10.

If desired, either or both of catheter sheath tube 34 and hemostasis valve partition 40 which are intended for use as replacement elements in sheath introducer 10 may be carried in their own, separate sealing caps similar to caps 22, 24, but without connection by tethers 20 to body portion 12. Thus, caps 22, 24 may be removed, and new caps carrying one or both of a new sheath tube 24 and a valve partition 40 may be snapped into place on body 12, for further convenience of use and assembly, and for better preservation of aseptic conditions.

Caps 22 and tethers 20 may also be used to provide a convenient suture site, for securance of the catheter sheath introducer in a desired position, if desired.

The above has been offered for illustrative purposes only, and is not intended to limit the scope of the invention of this application, which is as defined in the claims below.

That which is claimed is:

1. A catheter sheath introducer which comprises: a tubular body portion having opposed ends; a catheter sheath tube replaceably carried on one of said body portion ends; said catheter sheath tube being retained at said one end to first snap-fit, sealing attachment means, said sealing attachment means being removably connectable in sealing relation to said one body portion end and connected to said body portion by a tether; and a slit, elastomeric hemostasis valve partition carried on the other of said body portion ends.

2. The introducer of claim 1 in which said hemostasis valve partition is replaceably carried on the other body portion end.

3. The introducer of claim 2 in which said hemostasis valve partition is carried in second snap-fit attachment means connected to said other body portion end.

4. The introducer of claim 1 in which said body portion carries a laterally extending side port communicating with the interior of said body portion.

5. The introducer of claim 1 in which said hemostasis valve partition is carried in second snap-fit, sealing attachment means connectable in sealing relation to said other body portion end and connected to said body portion by a tether.

6. A catheter sheath introducer which comprises: a tubular body portion having opposed ends; a catheter sheath tube replaceably carried on one of said body portion ends; and a slit, elastomeric hemostasis valve partition replaceably carried on the other of said body portion ends, said catheter sheath tube being carried on said one end within first, snap-fit sealing attachment means connected to said one body portion end in snap-fit relation and also connected to said body portion by a tether, said body portion carrying a laterally extending side port communicating with the interior of said body portion.

7. The introducer of claim 6 in which said hemostasis valve portion is carried in second, snap-fit sealing attachment means connected to said other body portion end in snap-fit relation, said second attachment means being also connected to said body portion by a tether.

8. In the method of inserting a catheter sheath introducer into an artery of a patient, said catheter sheath introducer comprising a tubular body portion having opposed ends; a first catheter sheath tube carried on one of said body portion ends; and a first slit, elastomeric hemostasis valve partition carried on the other of said body portion ends, the improvement comprising, in combination: prior to said inserting of the catheter sheath introducer removing from said catheter sheath introducer at least one of said catheter sheath tube and said valve partition and replacing said removed sheath tube and/or valve partition with a second catheter sheath tube and/or a second elastomeric hemostasis valve partition to provide differing capabilities to said catheter sheath introducer from the capabilities of its original configuration.

9. The method of claim 8 in which said first catheter sheath tube is removed from a first snap-fit sealing attachment means connected to said body portion and attachable at said one body portion end, and said second catheter sheath tube is then connected to said first snap-fit sealing attachment means, after which said first snap-fit sealing attachment means is connected to said one body portion end.

10. The method of claim 9 in which said first hemostasis valve partition is removed from a second snap-fit sealing attachment means connected to said body portion and attachable at said other body portion end, and said second hemostasis valve partition is then connected to said second snap-fit sealing attachment means, after which said second snap-fit sealing attachment means is connected to said other body portion end.

11. In the method of inserting a catheter introducer into an artery of a patient, said catheter sheath introducer comprising a tubular body portion having opposed ends; a first catheter sheath tube carried on one of said body portion ends; and a first slit, elastomeric hemostasis valve partition carried on the other of said body portion ends, the improvement comprising, in combination: prior to said inserting of the catheter sheath introducer said first hemostasis valve partition is removed from a second snap-fit sealing attachment connected to said body portion and attachable at said other body portion end, and second hemostasis valve partition is then connected to said second snap-fit sealing attachment means, after which said second snap-fit sealing attachment means is connected to said other body portion end, to provide differing capabilities to said catheter sheath introducer from the capabilities of its original configuration.

* * * * *